United States Patent [19]
Casagrande et al.

[11] 4,381,305
[45] Apr. 26, 1983

[54] ETHYLENEDIAMINE DERIVATIVES AND PHARMACEUTICAL COMPOSITIONS CONTAINING SAME

[75] Inventors: Cesare Casagrande, Arese; Giorgio Ferrari, Milan, both of Italy

[73] Assignee: Simes S.p.A., Milan, Italy

[21] Appl. No.: 270,808

[22] Filed: Jun. 5, 1981

[30] Foreign Application Priority Data

Jun. 10, 1980 [IT] Italy .............................. 22677 A/80

[51] Int. Cl.³ ............... A61K 31/165; C07C 103/82; C07C 87/28; A61K 31/135
[52] U.S. Cl. .................................. 424/263; 424/266; 424/275; 424/285; 424/324; 424/330; 546/316; 546/323; 546/329; 546/334; 549/72; 549/74; 549/75; 549/487; 549/492; 549/495; 564/170; 564/176; 564/182; 564/185; 564/316; 564/319; 564/320; 564/166

[58] Field of Search ............... 564/166, 182, 185, 170, 564/176, 316, 320, 319; 260/347.3, 347.7; 546/316, 323, 329, 334; 549/72, 74, 75; 424/263, 266, 275, 285, 324, 330

[56] References Cited

U.S. PATENT DOCUMENTS 3,876,702  4/1975  Petersen et al. .................... 564/316

*Primary Examiner*—John M. Ford
*Assistant Examiner*—Bernard Dentz
*Attorney, Agent, or Firm*—Stevens, Davis, Miller & Mosher

[57] ABSTRACT

New derivatives of 1,2-ethylenediamine and salts thereof endowed with vascular antispasmodic and antiallergic activity; processes for preparing them, some new intermediates useful in their preparation and pharmaceutical compositions containing them.

5 Claims, No Drawings

ETHYLENEDIAMINE DERIVATIVES AND PHARMACEUTICAL COMPOSITIONS CONTAINING SAME

This invention provides novel compounds having useful antispasmodic activity on the smooth muscles; salts thereof, pharmaceutical compositions containing them as well as processes for preparing them and some new intermediates useful in their preparation. More particularly the novel compounds of this invention are useful as vascular antispasmodic agents and as antiallergic agents and may be represented by the following general formula

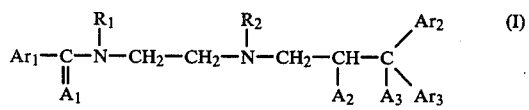

wherein:
- $R_1$ is hydrogen atom, a lower alkyl, or arylalkyl radical;
- $R_2$ is a lower alkyl radical;
- $Ar_1$ is an aryl, arylalkyl or heterocyclic radical which may be substituted;
- $Ar_2$ and $Ar_3$ are the same or different aryl radical which may be substituted;
- $A_1$ is an oxygen atom or 2 hydrogen atoms;
- $A_2$ is hydrogen;
- $A_3$ is a hydrogen atom, a hydroxyl radical or, together with $A_2$, is a bond of a double bond.

Moreover the present invention provides a process for preparing the novel compounds of formula I by reacting a Mannich base of formula

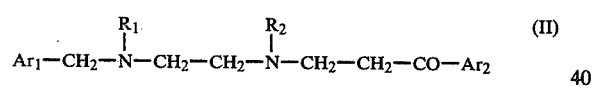

wherein $Ar_1$, $R_1$, $R_2$ and $Ar_2$ have the meanings defined above, with an aryl metallic derivative of formula $Ar_3Y$ (III) wherein $Ar_3$ has the meaning defined above and Y is a metal atom, preferably lithium, or a radical containing a metal atom such as Mg-Br, Mg-I, to give a tertiary alcohol of formula (Ia) according to the following SCHEME 1:

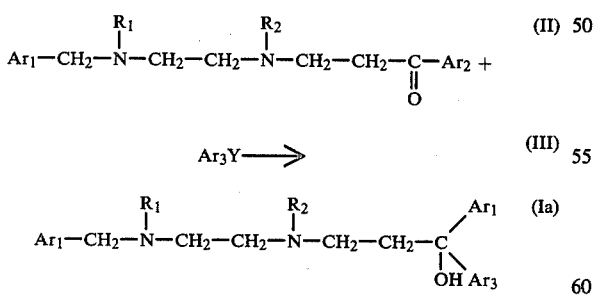

The compounds of formula Ia thus obtained may be processed further on to afford other products of formula I.

The reaction of Scheme 1 is preferably carried out in a solvent such as an aliphatic or cyclic ether, for example ethyl ether or tetrahydrofuran, at a temperature from $-30°$ C. to the boiling temperature of the solvent. The Mannich base of formula II is a further object of the present invention and may be prepared according to the following reaction scheme:

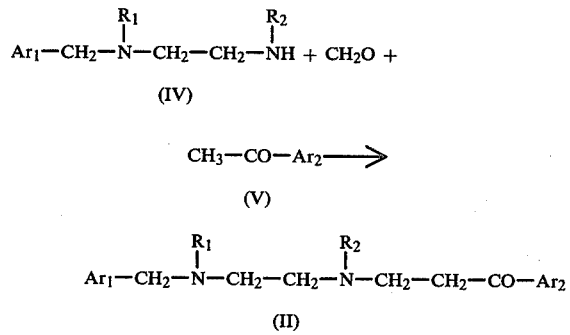

This reaction is carried out at a temperature between room temperature and the boiling temperature of the solvent and in the presence of an acid catalyst, for example hydrogen chloride.

Formaldehyde may be generated "in situ" by a suitable precursor such as trioxymethylene. Preferably the solvent used for this reaction is a polar solvent, for example an alcohol such as ethanol or isopropanol.

The compounds of formula III and V are well-known in the art.

The products of formula IV, when not already described in the art, may be prepared by conventional means according to the following SCHEME 2a:

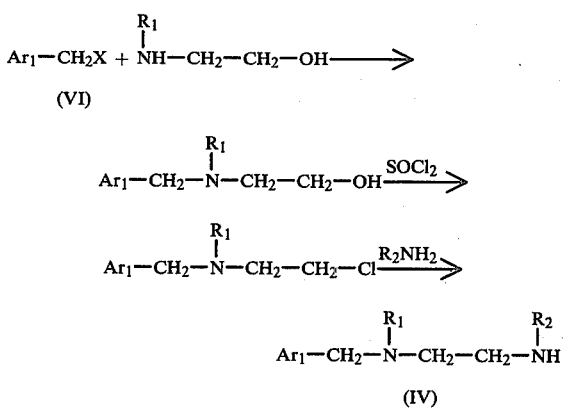

In formula VI $Ar_1$ has the meaning defined above and X is a halogen atom, methansulfonyloxy or toluenesulfonyloxy radical.

When $R_1$ and $R_2$ have the same meaning, the compound of formula IV, may be prepared also according to the following SCHEME 2b:

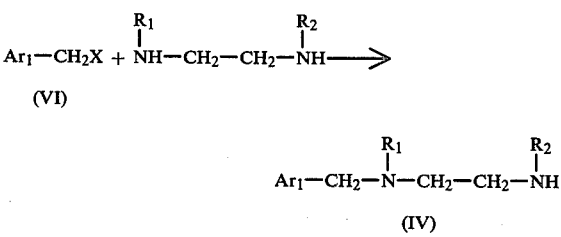

As stated above the tertiary alcohols of formula Ia may undergo one or more reactions to afford other products of formula I. For example a compound of formula Ia may undergo the hydrogenolysis of the Ar₁CH₂—group to give an amine of formula

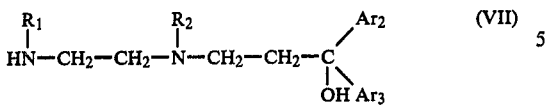

When R₁ is an arylalkyl radical as well the amine of formula VII in which R₁ is hydrogen is obtained.

Preferably the hydrogenolysis is carried out in a polar solvent such as an aliphatic alcohol or acetic acid, in the presence of a suitable catalyst such as palladium on charcoal. The hydrogenolysis is conveniently performed at a temperature between room temperature and 80° C. and at pressures between atmospheric pressure and 20 atm.

In turn, the amine VII may be substituted by reaction with a radical of formula

wherein $A_1$ and $Ar_1$ have the meanings defined above, to afford products of formula I.

When $A_1$ is two hydrogen atoms the reaction is carried out by heating the base of formula VII with a compound of formula VI at a temperature from 80° to 120° C. either without a solvent or in the presence of an inert solvent such as toluene.

When $A_1$ is an oxygen atom the reaction is carried out by acylating the base of formula VII with an acid of formula Ar₁COOH in which Ar₁ has the meaning defined above, or an active derivative thereof such as a halide or an anhydride. The acylation is preferably carried out in the presence of an inert solvent such as acetone, ethyl acetate or pyridine and at temperatures between room temperature and the boiling temperature of the solvent.

The amides thus obtained may be reduced, if desired, to the corresponding compounds of formula I in which $A_1$ represents 2 hydrogen atoms. The reducing agent may be an hydride such as lithium aluminum hydride or diborane. The reaction is carried out preferably at a temperature between room temperature and the boiling temperature of the solvent which may be an aliphatic or cyclic ether such as ethyl ether or tetrahydrofuran. Furthermore a tertiary alcohol of formula Ia ma be dehydrated to give a compound of formula I in which $A_2$ together with $A_3$ is a bond of a double bond. This reaction is preferably carried out at the boiling temperature of the solvent and in the presence of an acid catalyst such as hydrogen chloride. Suitable solvents are water or aliphatic alcohols.

The unsaturated product thus obtained may be hydrogenated to give a compound of formula I in which both $A_2$ and $A_3$ are hydrogen; the same compounds may be prepared also by hydrogenolysis of the hydroxyl group of the tertiary alcohols of formula Ia.

Both hydrogenation and hydrogenolysis are preferably carried out in the same reaction conditions described above for the preparation of the compounds of formula VII.

The hydrogenation step may be performed also by using Raney Nickel as catalyst and ethanol as a solvent at a pressure from 20 to 100 atm.

Some of the steps described above may be carried out also simultaneously. For example, according to the structure of the starting product, the use of a suitable catalyst such as palladium on charcoal affords the hydrogenolysis of the Ar₁CH₂—group together with the hydrogenolysis of the hydroxyl group or the hydrogenation of the double bond.

A further object of the present invention are the salts of the compounds of formula I with pharmaceutically acceptable inorganic or organic acids such as hydrogen chloride and maleic acid.

The compounds of the present invention are endowed with antispasmodic activity on the smooth muscles with has been established with the test of KCl—induced contraction of the rabbit's isolated aorta according to Godfraind and coll. (Arch. Int. Pharmacodyn., 172, 235, 1968).

The $ED_{50}$ ranges from 1.2 to 63 μg/ml.

As example, the $ED_{50}$ of some products of formula I are listed hereinafter:

N₁,N₂-dimethyl-N₁-benzyl-N₂-(3,3-diphenylallyl)-ethylenediamine dimaleate, 2.1 μg/ml N₁,N₂-dimethyl-N₁-benzyl-N₂-(3,3-diphenylpropyl)-ethylenediamine dimaleate, 4.6 μg/ml N₁,N₂-dimethyl-N₁-benzyl-N₂-(3,3-di-p-methoxyphenyl-3-hydroxypropyl)-ethylenediamine dimaleate, 5.2 μg/ml N₁,N₂-dimethyl-N₁-(3,4,5-trimethoxybenzyl)-N₂-(3,3-diphenylpropyl)-ethylenediamine dimaleate 1.3 μg/ml Moreover the compounds of formula I are endowed with a favorable tolerability.

The $LD_{50}$ of these compounds administered per os to mice are comprised between 300 and 2000 mg/kg.

The invention provides also pharmaceutical compositions comprising, as active ingredients, the compounds of formula I or the salts thereof.

These compositions may contain the active ingredient together with an organic or inorganic solid or liquid pharmaceutical excipient suitable for oral, parenteral or rectal administration. The pharmaceutical compositions may be in solid form such as tablets, dragées or capsules, or in liquid form as solutions, suspensions or emulsions; they may contain the usual carrier materials and may include auxiliary substances such as preserving, stabilizing, wetting or emulsifying agents, salts for regulating the osmotic pressure, buffers, dyestuffs or flavoring agents; they are prepared according to known methods and may further contain other valuable substances.

The following examples are given to illustrate the invention without limiting it in any way.

EXAMPLE 1

200 ml of concentrated hydrochloric acid, 100 g of acetophenone and 55 g of trioxymethylene are added to 100 g of N₁,N₂-dimethyl-N₁-benzylethylene amine dissolved in 1 l of isopropanol and 1 l of glacial acetic acid. The solution is refluxed for 4 hours under stirring, the solvent is removed under reduced pressure, the residue is dissolved in water and washed twice with 250 ml of chloroform. The aqueous layer is evaporated to dryness under reduced pressure; 300 ml of anhydrous ethanol are added and the solvent is removed under reduced pressure; the residue is dissolved in 2 l of anhydrous ethanol by heating. Upon standing, N₁,N₂-dimethyl-N₁-benzyl-N₂-(3-phenyl-3-oxopropyl)-ethylenediamine hydrochloride is obtained, m.p. 178°–180° C.

The thus obtained hydrochloride is treated with K$_2$CO$_3$, extracted with chloroform and the solvent is evaporated under reduced pressure to give the corresponding base.

To 57 g of this base dissolved in tetrahydrofuran an ethereal solution of 24 g of phenyllithium is slowly added.

The reaction mixture is stirred at room temperature for 12 hours and refluxed for a further 3 hours, then it is poured into ice and extracted with ethyl ether. The extract is dried over anhydrous sodium sulfate, filtered and evaporated. The residue dissolved in anhydrous ethanol is treated with an excess of an enthanolic solution of maleic acid. Upon standing crystalline N$_1$,N$_2$-dimethyl-N$_1$-benzyl-N$_2$-(3,3-diphenyl-3-hydroxypropyl)-ethylenediamine dimaleate is obtained, C$_{26}$H$_{32}$N$_2$O.2C$_4$H$_4$O$_4$, m.p. 180°–182° C.

The starting material N$_1$,N$_2$-dimethyl-N$_1$-benzylethylenediamine is prepared as follows:

340 g of benzylchloride dissolved in 200 ml of anhydrous toluene are slowly added to a stirred mixture of 400 g of monomethyl-amino-ethanol and 200 ml of anhydrous toluene.

After having refluxed for 5 hours and cooled, 200 ml of water and 300 ml of toluene are added. The organic layer is separated, dried over anhydrous sodium sulfate and evaporated. The residue is distilled: N-methyl-N-benzylaminoethanol is obtained; b.p. 105°–110° C. at 2 mmHg.

330 g of the thus obtained product are dissolved in 1 l of anhydrous toluene and then 286 g of thionyl-chloride are slowly added. The reaction mixture is heated to 90° C. for 1 hour, then cooled, filtered and washed with toluene to afford N-benzyl-N-methyl-2-chloro-ethylamine dihydrochloride (m.p. 141°–143° C.) which is taken up in 800 ml of anhydrous ethanol and treated with 1500 ml of 30% (w/v) ethanolic solution of methylamine. After heating to 50° C. for 24 hours, the solvent is removed under reduced pressure; the residue is taken up in 60 ml of 40% sodium hydroxide and exhaustively extracted with chloroform. The extracts are dried over anhydrous sodium sulfate and evaporated under reduced pressure. The residue is distilled (b.p. 95°–100° C. at 0.5 mmHg) to give N$_1$,N$_2$-dimethyl-N$_1$-benzylethylenediamine.

By analogous procedures but using

N$_1$-methyl-N$_1$-benzyl-N$_2$-ethyl-ethylenediamine
N$_1$-methyl-N$_1$-benzyl-N$_2$-propyl-ethylenediamine
N$_1$-methyl-N$_1$-benzyl-N$_2$-butyl-ethylenediamine
N$_1$-methyl-N$_2$-dibenzyl-ethylenediamine in place of N$_1$,N$_2$-dimethyl-N$_1$-benzyl-ethylenediamine the following compounds have been respectively prepared:

N$_1$-methyl-N$_1$-benzyl-N$_2$-ethyl-N$_2$-(3,3-diphenyl-3-hydroxypropyl)-ethylenediamine dimaleate, m.p. 159°–161° C., C$_{27}$H$_{34}$N$_2$O.2C$_4$H$_4$O$_4$.
N$_1$-methyl-N$_1$-benzyl-N$_2$-propyl-N$_2$-(3,3-diphenyl-3-hydroxypropyl)-ethylenediamine dimaleate, m.p. 167°–169° C., C$_{28}$H$_{36}$N$_2$O.2C$_4$H$_4$O$_4$
N$_1$-methyl-N$_1$-benzyl-N$_2$-butyl-N$_2$-(3,3-diphenyl-3-hydroxypropyl)-ethylenediamine dimaleate, m.p. 165°–166° C., C$_{29}$H$_{38}$N$_2$O.2C$_4$H$_4$O$_4$.
N$_1$-dibenzyl-N$_2$-methyl-N$_2$-(3,3-diphenyl-3-hydroxypropyl)-ethylenediamine (oil), C$_{32}$H$_{36}$N$_2$O

EXAMPLE 2

80 g of N$_1$,N$_2$-dimethyl-N$_1$-benzyl-N$_2$-(3,3-diphenyl-3-hydroxypropyl)-ethylenediamine bimaleate obtained according to example 1 are dissolved in 500 ml of anhydrous ethanol, treated with 400 ml of 20% ethanolic solution of anhydrous hydrogen chloride and refluxed for 4 hours. The solvent is removed under reduced pressure. The residue is dissolved in water and washed twice with ether, the aqueous layer is made basic with ammonium hydroxide and extracted with chloroform. The extract is dried over anhydrous sodium sulfate and evaporated, the residue is dissolved in about 200 ml of ethanol and treated with an excess of an ethanolic solution of maleic acid.

Upon standing, crystalline N$_1$,N$_2$-dimethyl-N$_1$-benzyl-N$_2$-(3,3-diphenylallyl)-ethylenediamine bimaleate is obtained, C$_{26}$H$_{30}$N$_2$.2C$_4$H$_4$O$_4$, m.p. 170°–171° C.

Alternatively, the base is dissolved in ethylacetate and treated with anhydrous hydrogen chloride to afford amorphous hygroscopic N$_1$,N$_2$-dimethyl-N$_1$-benzyl-N$_2$-(3,3-diphenylallyl)-ethylenediamine dihydrochloride which may be further reacted (see example 3).

By analogous procedures but using

N$_1$-methyl-N$_1$-benzyl-N$_2$-ethyl-N$_2$-(3,3-diphenyl-3-hydroxypropyl)-ethylenediamine dimaleate (see example 1)
N$_1$-dibenzyl-N$_2$-methyl-N$_2$-(3,3-diphenyl-3-hydroxypropyl)-ethylenediamine (see example 1)

in place of N$_1$,N$_2$-dimethyl-N$_1$-benzyl-N$_2$-(3,3-diphenyl-3-hydroxypropyl)-ethylenediamine dimaleate the following compounds have been prepared:

N$_1$-methyl-N$_1$-benzyl-N$_2$-ethyl-N$_2$-(3,3-diphenylallyl)-ethylenediamine dimaleate, m.p. 131°–133° C., C$_{27}$H$_{32}$N$_2$.2C$_4$H$_4$O$_4$
N$_1$-dibenzyl-N$_2$-methyl-N$_2$-(3,3-diphenylallyl)-ethylenediamine (oil), C$_{31}$H$_{34}$N$_2$

EXAMPLE 3

A mixture of 90 g of N$_1$,N$_2$-dimethyl-N$_1$-benzyl-N$_2$-(3,3-diphenylallyl)-ethylenediamine dihydrochloride, prepared according to example 2, 400 ml of 95% ethanol and 9 g of 10% palladium-charcoal is hydrogenated at 4 atm until the hydrogen absorption is complete. The catalyst is removed by filtration, then the solvent is evaporated under reduced pressure. The residue is dissolved in 150 ml of water, washed with ethyl ether and the aqueous layer is evaporated to dryness under reduced pressure. Ethanol is added and after evaporation of the solvent, the residue is taken up in about 200 ml of acetone and allowed to stand for 24 hours; N$_1$,N$_2$-dimethyl-N$_2$-(3,3-diphenylpropyl)-ethylenediamine dihydrochloride cristalizes (m.p. 161°–164° C.). The free base is obtained from the hydrochloride by treatment with sodium hydroxide, extraction with chloroform and evaporation of the solvent.

The base is dissolved in 200 ml of toluene, treated with 40 g of benzyl-iodide and refluxed for 2 hours; then it is cooled, made basic with ammonium hydroxide, extracted with ethylacetate and evaporated. The residue is taken up in anhydrous ethanol, made acid with an excess of ethanolic solution of maleic acid; upon standing, crystalline N$_1$,N$_2$-dimethyl-N$_1$-benzyl-N$_2$-(3,3-diphenylpropyl)-ethylenediamine dimaleate is obtained, C$_{26}$H$_{32}$N$_2$.2C$_4$H$_4$O$_4$, m.p. 162°–164° C.

EXAMPLE 4

Following the procedure set out in Example 3 but using an equivalent amount of p-chlorobenzyl-iodide in place of benzyl-iodide used therein, $N_1,N_2$-dimethyl-$N_1$-(p-chlorobenzyl)-$N_2$-(3,3-diphenylpropyl)-ethylenediamine dimaleate is obtained, m.p. 170°–171° C., $C_{26}H_{31}ClN_2.2C_4H_4O_4$

EXAMPLE 5

40 g of $N_1,N_2$-dimethyl-$N_2$-(3,3-diphenylpropyl)-ethylenediamine dihydrochloride, prepared according to Example 3, in 400 ml of anhydrous pyridine are treated with 24 g of p-chlorobenzoyl chloride. The reaction mixture is stirred at room temperature for 7 hours, then 40 ml of water are added and the solvent is removed under reduced pressure. The residue is taken up in water, the pH is adjusted to 9 with sodium hydroxide and the extracts obtained by extraction with chloroform are dried on anhydrous sodium sulfate and evaporated. The residue is chromatographed on silica gel by using methylene/methanol 95:5 as eluant to yield pure $N_1,N_2$-dimethyl-$N_1$-(p-chlorobenzoyl)-$N_2$-(3,3-diphenylpropyl)-ethylenediamine as oil (TLC, eluant methylenechloride/methanol/water-88:11:1; iodine detection)

Analysis % N calculated 6.65 found 6.31. Cl calculated 8.42 found 8.73.

Mass spectrum m/e 420 (M+)

An analogous procedures $N_1,N_2$-dimethyl-$N_2$-(3,3-diphenylpropyl)-ethylenediamine is reacted with suitable carboxylic acid chlorides to afford the following compounds:

$N_1,N_2$-dimethyl-$N_1$-(m-chlorobenzoyl)-$N_2$-(3,3-diphenylpropyl)-ethylenediamine, $C_{26}H_{29}ClN_2O$ $N_1,N_2$-dimethyl-$N_1$-(3,4,5-trimethoxybenzoyl)-$N_2$-(3,3-diphenylpropyl)-ethylenediamine, $C_{29}H_{38}N_2O_4$ $N_1,N_2$-dimethyl-$N_1$-(3,4-dimethoxybenzoyl)-$N_2$-(3,3-diphenylpropyl)-ethylenediamine, $C_{28}H_{34}N_2O_3$ $N_1,N_2$-dimethyl-$N_1$-(p-nitrobenzoyl)-$N_2$-(3,3-diphenylpropyl)-ethylenediamine, $C_{26}H_{29}N_3O_3$ $N_1,N_2$-dimethyl-$N_1$-(m-nitrobenzoyl)-$N_2$-(3,3-diphenylpropyl)-ethylenediamine, $C_{26}H_{29}N_3O_3$ $N_1,N_2$-dimethyl-$N_1$-(2-furanylcarbonyl)-$N_2$-(3,3-diphenylpropyl)-ethylenediamine, $C_{24}H_{28}N_2O_2$ $N_1,N_2$-dimethyl-$N_1$-(3-nicotinoyl)-$N_2$-(3,3-diphenylpropyl)-ethylenediamine, $C_{25}N_{29}N_3O$ $N_1,N_2$-dimethyl-$N_1$-(isonicotinoyl)-$N_2$-(3,3-diphenylpropyl)-ethylenediamine, $C_{25}H_{29}N_3O$ $N_1,N_2$-dimethyl-$N_1$-(2-thienylcarbonyl)-$N_2$-(3,3-diphenylpropyl)-ethylenediamine, $C_{24}H_{28}N_2SO$ $N_1,N_2$-dimethyl-$N_1$-(3,4-dimethoxyphenylacetyl)-$N_2$-(3,3-diphenylpropyl)-ethylenediamine, $C_{29}H_{36}N_2O_3$

EXAMPLE 6

10 g of $N_1,N_2$-dimethyl-$N_1$-(p-chlorobenzoyl)-$N_2$-(3,3-diphenylpropyl)-ethylenediamine obtained according to example 5 are dissolved in 60 ml of tetrahydrofuran and are slowly added to a vigorously stirred suspension of 1.2 g of lithium aluminum hydride in 20 ml of tetrahydrofuran. The mixture is stirred for 4 hours at room temperature, the excess of hydride is removed, the mixture is poured in water, extracted with chloroform, dried over anhydrous sodium sulfate and evaporated. The residue is dissolved in anhydrous ethanol and treated with an excess of an ethanolic solution of maleic acid. upon standing, $N_1,N_2$-dimethyl-$N_1$-(p-chlorobenzyl)-$N_2$-(3,3-diphenylpropyl)-ethylenediamine dimaleate is obtained, m.p. 169°–171° C.

By reacting in a similar way the amides of the example 5, the following compounds are prepared:

$N_1,N_2$-dimethyl-$N_1$-(m-chlorobenzyl)-$N_2$-(3,3-diphenylpropyl)-ethylenediamine dimaleate, $C_{26}H_{31}N_2Cl.2C_4H_4O_4$, m.p. 153°–154° C.

$N_1,N_2$-dimethyl-$N_1$-(3,4,5-trimethoxybenzyl)-$N_2$-(3,3-diphenylpropyl)-ethylenediamine dimaleate, $C_{29}H_{38}N_2O_3.2C_4H_4O_4$, m.p. 159°–162° C.

$N_1,N_2$-dimethyl-$N_1$-(3,4-dimethoxybenzyl)-$N_2$-(3,3-diphenylpropyl)-ethylenediamine dimaleate, $C_{28}H_{36}N_2O_2$, m.p. 162°–163° C.

$N_1,N_2$-dimethyl-$N_1$-(2-furanylmethyl)-$N_2$-(3,3-diphenylpropyl)-ethylenediamine dimaleate, $C_{24}H_{30}N_2O.2C_4H_4O_4$, m.p. 150°–152° C.

$N_1,N_2$-dimethyl-$N_1$-(3-pyridinylmethyl)-$N_2$-(3,3-diphenylpropyl)-ethylenediamine dimaleate, $C_{25}H_{31}N_3.2C_4H_4O_4$, m.p. 139°–141° C.

$N_1,N_2$-dimethyl-$N_1$-(4-pyridinylmethyl)-$N_2$-(3,3-diphenylpropyl)-ethylenediamine dimaleate, $C_{25}H_{31}N_3.2C_4H_4O_4$, m.p. 124°–125° C.

$N_1,N_2$-dimethyl-$N_1$-(2-thienylmethyl)-$N_2$-(3,3-diphenylpropyl)-ethylenediamine dimaleate, $C_{24}H_{30}N_2O_5.2C_4H_4O_4$, m.p. 162°–164° C.

$N_1,N_2$-dimethyl-$N_1$-[2-(3,4-dimethoxyphenyl)-ethyl]-$N_2$-(3,3-diphenylpropyl)-ethylenediamine dimaleate, $C_{29}H_{38}N_2O_2.2C_4H_4O_4$, m.p. 142°–144° C.

EXAMPLE 7

20 g of $N_1,N_2$-dimethyl-$N_2$-(3,3-diphenylpropyl)-ethylenediamine dihydrochloride, prepared according to the procedure described in Example 3, 200 ml of anhydrous pyridine and 12 g of p-methoxybenzoylchloride are stirred for 5 hours at room temperature. 20 ml of water are added and the reaction mixture is evaporated to dryness under reduced pressure. The residue is taken up in water, adjusted to pH 9 with sodium hydroxide and extracted with chloroform. The extracts are dried over anhydrous sodium sulfate and evaporated. The residue is chromatographed on silica gel by using methylenechloride/methanol 95:5 as eluant to yield 17 g of pure $N_1,N_2$-dimethyl-$N_1$-(p-methoxybenzoyl)-$N_2$-(3,3-diphenylpropyl)-ethylenediamine as an oil (TLC on silica gel, eluant methylenechloride/methanol/water 88:11:1; iodine detection)

Analysis % N calculated 6.72 found 6.58

Mass spectrum: m/e=416 (M+)

EXAMPLE 8

Following the procedure described in Example 6, $N_1,N_2$-dimethyl-$N_1$-(p-methoxybenzoyl)l-$N_2$-(3,3-diphenylpropyl)-ethylenediamine, prepared according to Example 7, is reduced by means of lithium-aluminumhydride to give $N_1,N_2$-dimethyl-$N_1$-(p-methoxybenzyl)-$N_2$-(3,3-diphenylpropyl)-ethylenediamine dimaleate.

$C_{27}H_{34}N_2O.2C_4H_4O_4$, m.p. 167°–168° C.

EXAMPLE 9

178 g of $N_1,N_2$-dimethyl-$N_1$-benzylethylenediamine, 1 l of isopropanol, 1 l of glacial acetic acid and 320 ml of concentrated hydrochloric acid are reacted with 180 g of p-methoxyacetophenone and 100 g of trioxymethylene at the reflux for 4 hours under stirring. The solvent is removed under reduced pressure, the residue is taken up in 1.2 l of water and the solution thus obtained is washed with chloroform. The pH of the aqueous layer is adjusted to 9 with sodium hydroxide, extracted with chloroform, washed once with water, dried over anhydrous sodium sulfate and evaporated to dryness. The residue is dissolved with anhydrous ethanol and treated with a solution of hydrogen chloride in ethanol to give $N_1,N_2$-dimethyl-$N_1$-benzyl-$N_2$-(3-p-methoxyphenyl-3-oxo-propyl)-ethylenediamine dihydrochloride, m.p. 179°–181° C.

From the thus obtained dihydrochloride the corresponding base is prepared by addition of $K_2CO_3$, extraction with chloroform and evaporation of the solvent under reduced pressure. 135 g of the thus obtained base are dissolved in 200 ml of anhydrous tetrahydrofuran and slowly added to a stirred ethereal solution of 66 g of phenyllithium in nitrogen atmosphere. The reaction mixture is allowed to stand at room temperature for 2 hours, then it is poured into ice, extracted with ethylacetate, washed once with water, dried on anhydrous sodium sulfate and evaporated. The residue is dissolved in anhydrous ethanol and treated with an excess of a solution of maleic acid in ethanol. Upon standing, crystalline $N_1,N_2$-dimethyl-$N_1$-benzyl-$N_2$-(3-phenyl-3-p-methoxyphenyl-3-hydroxypropyl)-ethylenediamine dimaleate is obtained.

$C_{27}H_{34}N_2O_2.2C_4H_4O_4$, m.p. 163°–165° C.

By analogous procedures but using p-chloroacetophenone and p-methyl-acetophenone in place of p-methoxyacetophenone the following compounds are respectively obtained:

$N_1,N_2$-dimethyl-$N_1$-benzyl-$N_2$-(3-p-chlorophenyl-3-phenyl-3-hydroxypropyl)-ethylenediamine dimaleate, $C_{26}H_{31}ClNO.2C_4H_4O_4$, m.p. 170°–172° C.
$N_1,N_2$-dimethyl-$N_1$-benzyl-$N_2$-(3p-methylphenyl-3-phenyl-3-hydroxypropyl)-ethylenediamine dimaleate, $C_{27}H_{34}N_2O.2C_4H_4O_4$, m.p. 182°–184° C.

EXAMPLE 10

A mixture of 13 g of p-bromo-anisole and 50 ml of anhydrous ether is slowly added under stirring to an ethereal solution of 4.6 g of n-butyllithium in nitrogen atmosphere at −30° C.

The mixture is allowed to stand for 15 minutes at room temperature, then 15.5 g of $N_1,N_2$-dimethyl-$N_1$-benzyl-$N_2$-(3-phenyl-3-oxopropyl)-ethylenediamine base, prepared according to Example 1, and dissolved in 50 ml of anhydrous ethyl ether are added in about 10 minutes and under slight reflux. The reaction mixture is stirred at room temperature for 24 hours, poured into ice, extracted with chloroform, washed once with water, dried over anhydrous sodium sulfate and evaporated to dryness. The residue is chromatographed on silica gel by eluating with chloroform; the thus obtained product is dissolved in anhydrous ethanol and treated with an excess of a solution of maleic acid in ethanol; upon standing, crystalline $N_1,N_2$-dimethyl-$N_1$-benzyl-$N_2$-(3-phenyl-3-p-methoxyphenyl-3-hydroxypropyl)-ethylenediamine dimaleate is obtained, m.p. 163°–165° C., $C_{27}H_{34}N_2O_2.2C_4H_4O_4$.

When magnesium and p-fluoro-benzene are used in place of p-bromo-anisole and n-butyllithium and the reaction is carried out in an analogous way, $N_1,N_2$-dimethyl-$N_2$-(3-p-fluorophenyl-3-phenyl-3-hydroxypropyl)-ethylenediamine dimaleate is obtained, $C_{26}H_{31}FNO_2.2C_4H_4O_4$, m.p. 181°–182° C.

By analogous procedure but using $N_1,N_2$-dimethyl-$N_1$-benzyl-$N_2$-(3-p-methoxyphenyl-3-oxopropyl)-ethylenediamine (as prepared in the example 9) in place of $N_1,N_2$-dimethyl-$N_1$-benzyl-$N_2$-(3-p-phenyl-3-oxopropyl)-ethylenediamine with proper magnesium derivatives, the following compounds are obtained:

$N_1,N_2$-dimethyl-$N_1$-benzyl-$N_2$-(3,3-di-p-methoxyphenyl-3-hydroxypropyl)-ethylenediamine dimaleate, $C_{28}H_{36}N_2O_3.2C_4H_4O_4$, m.p. 169°–172° C.
$N_1,N_2$-dimethyl-$N_1$-benzyl-$N_2$-(3-p-fluorophenyl-3-p-methoxyphenyl-3-hydroxypropyl)-ethylenediamine dimaleate, $C_{27}H_{33}FN_2O_2.2C_4H_4O_4$, m.p. 165°–166° C.
$N_1,N_2$-dimethyl-$N_1$-benzyl-$N_2$-(3-p-chlorophenyl-3-p-methoxyphenyl-3-hydroxpropyl)-ethylenediamine dimaleate, $C_{27}H_{33}ClN_2O_2.2C_4H_4O_4$, m.p. 166°–168° C.
$N_1,N_2$-dimethyl-$N_1$-benzyl-$N_2$-(3-p-methylphenyl-3-p-methoxyphenyl-3-hydroxypropyl)-ethylenediamine dimaleate, $C_{28}N_{36}N_2O_2.2C_4H_4O_4$, m.p. 165°–167° C.

EXAMPLE 11

100 g of $N_1,N_2$-dimethyl-$N_1$-benzyl-$N_2$-(3-phenyl-3-p-methoxyphenyl-3-hydroxypropyl)-ethylenediamine dimaleate, prepared according to Example 9 or 10, and 600 ml of a 25% (w/v) ethanolic solution of anhydrous hydrogen chloride are refluxed for 2 hours. The solvent is evaporated under reduced pressure, the residue is taken up in water, the pH is adjusted to 9 with sodium hydroxide and it is extracted with chloroform. The extracts are washed once with water, dried over anhydrous sodium sulfate and evaporated to dryness. The residue is dissolved in anhydrous ethanol and treated with an excess of an ethanolic solution of maleic acid. Upon standing, crystalline $N_1,N_2$-dimethyl-$N_1$-benzyl-$N_2$-(3-phenyl-3-p-methoxyphenylallyl)-ethylenediamine dimaleate is obtained.

$C_{27}H_{32}N_2O.2C_4H_4O_4$, m.p. 170°–172° C.

EXAMPLE 12

A mixture of 30 g of $N_1,N_2$-dimethyl-$N_1$-benzyl-$N_2$-(3-phenyl-3-p-methoxyphenylally)-ethylenediamine dimaleate prepared according to Example 11, of 600 ml of 95% ethanol and 5 g of 10% palladium on charcoal is hydrogenated at 4 atm for 6 hours. The catalyst is filtered off and the solvent is evaporated under reduced pressure. The residue is taken up in the slightest quantity of water as possible and, after having adjusted the pH to 9 sodium hydroxyde, it is extracted with chloroform. The extracts are dried over anhydrous sodium sulfate and evaporated to dryness. The residue is dissolved in anhydrous ethanol and treated with an excess of an ethanolic solution of maleic acid. Upon standing crystalline $N_1,N_2$-dimethyl-$N_2$-(3-phenyl-3-p-methoxyphenylpropyl)-ethylenediamine dimaleate is obtained (m.p. 123°–125° C.). The product thus obtained is dissolved in 200 ml of anhydrous pyridine and reacted with 20 ml of benzoylchloride. The mixture is allowed to stand at room temperature for 24 hours, then 20 ml of water are added and the solvent is removed under reduced pressure. The residue is taken up in water and after having adjusted the pH to 9 with sodium hydroxide, it is extracted with chloroform; the extracts are washed once with water, dried over anhydrous sodium sulfate and evaporated to dryness. $N_1,N_2$-dimethyl-$N_1$-benzoyl-$N_2$-(3-phenyl-3-methoxyphenylpropyl)-ethylenediamine thus obtained is dissolved into 200 ml of tetrahydrofuran and this solution is added slowly to a suspension of 4.8 g of lithium aluminum hydride in 60 ml of tetrahydrofuran under stirring. The non-reacted hydride is removed; after having added water the solution is extracted with chloroform and the extract is washed once with water, dried over anhydrous sodium sulfate and evaporated. The residue is dissolved in anhydrous ethanol and treated with an excess of an ethanolic solution of maleic acid. Upon standing, crystalline $N_1,N_2$-dimethyl-$N_1$-benzyl-$N_2$-(3-phenyl-3-p-methoxyphenylpropyl)-ethylenediamine dimaleate is obtained. $C_{27}H_{34}N_2O.2C_4H_4O_4$, m.p. 158°–160° C.

By analogous procedure but using $N_1$-dibenzyl-$N_2$-methyl-$N_2$-(3,3-diphenyiallyl)-ethylenediamine in place of $N_1,N_2$-dimethyl-$N_1$-benzyl-$N_2$-(3-phenyl-3-p-methoxyphenylallyl)-ethylenediamine, N-methyl-N-(3,3-phenylpropyl)-ethylenediamine dimaleate is obtained.

This primary amine (as free base) may react with suitable chlorides as described above to afford $N_1$-(3-nitrobenzoyl)-$N_2$-methyl-$N_2$-methyl-$N_2$-(3,3-diphenylpropyl)-ethylenediamine (oil), $C_{25}H_{27}N_3O_3$ $N_1$-(3,4,5-trimethoxybenzoyl)-$N_2$-methyl-$N_2$-(3,3-diphenylpropyl)-ethylenediamine dimaleate $C_{28}H_{34}N_2O_4.2C_4H_4O_4$, m.p. 149°–150° C.

$N_1$-(isonicotinoyl)-$N_2$-methyl-$N_2$-(3,3-diphenylpropyl)-ethylenediamine (oil), $C_{24}H_{26}N_3O$ These two last compounds may be reduced according to the above described procedure to give $N_1$-(3,4,5-trimethoxybenzyl)-$N_2$-methyl-$N_2$-(3,3-diphenylpropyl)-ethylenediamine dimaleate, $C_{28}H_{36}N_2O_3.2C_4H_4O_4$, m.p. 140°–142° C.

$N_1$-(4-pyridinylmethyl)-$N_2$-methyl-$N_2$-(3,3-diphenylpropyl)-ethylenediamine dimaleate, $C_{24}H_{29}N_3.2C_4H_4O_4$

EXAMPLE 13

25 g of $N_1,N_2$-dimethyl-$N_1$-benzyl-$N_2$-(3,3-diphenyl-3-hydroxypropyl)-ethylenediamine dimaleate obtained according to Example 1, are dissolved into 400 ml of methanol and are reacted in the presence of 5 g of 5% palladium on charcoal at 5 atm for 5 hours. The catalyst is filtered off and the solution is evaporated to dryness. The residue is taken up in water, basified with ammonium hydroxide and extracted with ether. After drying over anhydrous sodium sulphate, it is filtered and evaporated, then the residue is dissolved in ethyl acetate and treated with hydrogen chloride in ethyl ether. After addition of 10% ethanol it is allowed to stand. Crystalline $N_1,N_2$-dimethyl-$N_2$-(3,3-diphenyl-3-hydroxypropyl)-ethylenediamine dihydrochloride is obtained, m.p. 191°–193° C.

3.3 g of this compound are dissolved in 100 ml of anhydrous ethanol and refluxed for 5 hours with a 20% (w/v) solution of hydrogen chloride in ethanol. After evaporation of the solvent, the residue is taken up in water, made basic with ammonium hydroxide, extracted with chloroform, dried over sodium sulfate and filtered.

After removal of the solvent the residue is taken up in anhydrous ethanol and acidified with an excess of ethanolic solution of maleic acid to give crystalline $N_1,N_2$-dimethyl-$N_2$-(3,3-diphenylallyl)-ethylenediamine dimaleate, $C_{19}H_{24}N_3.2C_4H_4O_4$, m.p. 154°–156° C.

This compound may be obtained directly from the starting material carrying out the hydrogenolysis in the presence of a mineral acid. The free base may further react with 3,4,5-trimethoxy-benzoylchloride according to the procedure of example 5 to give $N_1,N_2$-dimethyl-$N_1$-(3,4,5-trimethoxybenzoyl)-$N_2$-(3,3-diphenylallyl)-ethylenediamine. This compound is reacted according to the procedure described in example 6 to afford $N_1,N_2$-dimethyl-$N_1$-(3,4,5-trimethoxybenzyl)-$N_2$-(3,3-diphenylallyl)-ethylenediamine dimaleate, m.p. 175°–177° C.

What is claimed is:

1. A compound of formula $$Ar_1-\underset{\underset{A_1}{\|}}{C}-\underset{\underset{}{R_1}}{N}-CH_2-CH_2N-CH_2-\underset{\underset{A_3}{|}}{CH}-C\diagup^{Ar_2}_{\diagdown Ar_3}$$ (I)

wherein
$R_1$ is a hydrogen atom, a lower alkyl, or an arylalkyl radical;
$R_2$ is a lower alkyl radical;
$Ar_1$ is an aryl radical which may be substituted by one or more radicals selected from the group consisting of nitro, chlorine and methoxy, an arylalkyl radical, or a heterocyclic radical selected from the group consisting of furanyl, thienyl and pyridinyl;
$Ar_2$ and $Ar_3$ are the same or different aryl radicals which may be substituted by one or more radicals selected from the group consisting of chlorine, fluorine, methyl and methoxy;
$A_1$ is an oxygen atom or 2 hydrogen atoms;
$A_2$ is hydrogen;
$A_3$ is a hydrogen atom, a hydroxyl radical, or, together with $A_2$, is a bond of a double bond.

2. A pharmaceutically acceptable salt of a compound as claimed in claim 1, with an organic or inorganic acid.

3. A compound as defined in claim 1, wherein $Ar_1$ is a heterocyclic radical.

4. A pharmaceutical composition comprising a vascular antispasmodic or antiallergic amount of a compound of formula $$Ar_1-\underset{\underset{A_1}{\|}}{C}-\underset{\underset{}{R_1}}{N}-CH_2-CH_2-\underset{\underset{}{R_2}}{N}-CH_2-\underset{\underset{A_3}{|}}{CH}-C\diagup^{Ar_2}_{\diagdown Ar_3}$$

wherein
$R_1$ is a hydrogen atom, a lower alkyl, or an arylalkyl radical;
$R_2$ is a lower alkyl radical;
$Ar_1$ is an aryl radical which may be substituted by one or more radicals selected from the group consisting of nitro, chlorine and methoxy, an arylalkyl radical, or a heterocyclic radical selected from the group consisting of furanyl, thienyl and pyridinyl;
$Ar_2$ and $Ar_3$ are the same or different aryl radicals which may be substituted by one or more radicals selected from the group consisting of chlorine, fluorine, methyl and methoxy;
$A_1$ is an oxygen atom or 2 hydrogen atoms;
$A_2$ is hydrogen;
$A_3$ is a hydrogen atom, a hydroxyl radical, or, together with $A_2$, is a bond of a double bond,
or a pharmaceutically acceptable salt thereof together with a pharmaceutically acceptable excipient.

5. A pharmaceutical composition as defined in claim 4, wherein $Ar_1$ is a heterocyclic radical.

* * * * *

UNITED STATES PATENT AND TRADEMARK OFFICE
CERTIFICATE OF CORRECTION

PATENT NO. : 4,381,305
DATED : April 26, 1983
INVENTOR(S) : Cesare CASAGRANDE, et al.

It is certified that error appears in the above-identified patent and that said Letters Patent is hereby corrected as shown below:

Column 12,
In claim 4 the formula should read as follows:

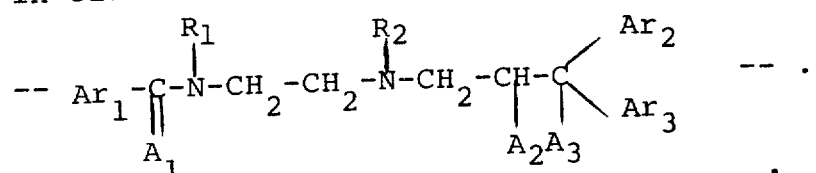

Signed and Sealed this

Fifth Day of March 1985

[SEAL]

Attest:

DONALD J. QUIGG

Attesting Officer   Acting Commissioner of Patents and Trademarks